US010265330B2

(12) United States Patent
Froyman et al.

(10) Patent No.: US 10,265,330 B2
(45) Date of Patent: Apr. 23, 2019

(54) PHARMACEUTICAL COMPOSITIONS AND TREATMENT OF MASTITIS

(71) Applicant: BAYER ANIMAL HEALTH GMBH, Leverkusen (DE)

(72) Inventors: Robrecht Froyman, Heusden-Zolder (BE); Heinz-Georg Wetzstein, Leverkusen (DE); Kristine Fraatz, Burscheid (DE); Wolfgang Wiehl, Köln (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 260 days.

(21) Appl. No.: 14/407,455

(22) PCT Filed: Jun. 25, 2013

(86) PCT No.: PCT/EP2013/063310
§ 371 (c)(1),
(2) Date: Dec. 11, 2014

(87) PCT Pub. No.: WO2014/001353
PCT Pub. Date: Jan. 3, 2014

(65) Prior Publication Data
US 2015/0164926 A1 Jun. 18, 2015

Related U.S. Application Data

(60) Provisional application No. 61/666,312, filed on Jun. 29, 2012.

(51) Int. Cl.
| | | |
|---|---|---|
| *A61K 31/665* | (2006.01) | |
| *A61K 31/43* | (2006.01) | |
| *A61K 31/496* | (2006.01) | |
| *A61K 31/546* | (2006.01) | |
| *A61K 31/706* | (2006.01) | |

(52) U.S. Cl.
CPC ............ *A61K 31/665* (2013.01); *A61K 31/43* (2013.01); *A61K 31/496* (2013.01); *A61K 31/546* (2013.01); *A61K 31/706* (2013.01)

(58) Field of Classification Search
None
See application file for complete search history.

(56) References Cited

U.S. PATENT DOCUMENTS

| | | | | |
|---|---|---|---|---|
| 4,034,099 | A * | 7/1977 | Bryan et al. .................. | 514/199 |
| 4,210,635 | A | 7/1980 | Imanaka et al. | |
| 4,330,529 | A * | 5/1982 | Imanaka ................ | A61K 31/66 424/114 |
| 8,449,916 | B1 * | 5/2013 | Bellaire ................... | A61K 9/14 424/489 |

FOREIGN PATENT DOCUMENTS

| | | |
|---|---|---|
| CN | 101744827 A | 6/2010 |
| CN | 101879172 A | 11/2010 |
| CN | 103079568 A | 5/2013 |
| EP | 2018864 A1 | 1/2009 |
| JP | S62129217 | 6/1987 |
| WO | 2012/004324 A1 | 1/2012 |
| WO | 2012/154076 A1 | 11/2012 |
| WO | 2014/001353 A1 | 1/2014 |

OTHER PUBLICATIONS

Mikuniya et al., "Synergistic Effects of Fosfomycin and Fluoroquinones against Psuedomonas aeruginosa growing on biofilnn", Acta Medica Okayama, 59, pp. 209-216, 2005—abstract.*
Brouillette, "Mouse mastitis model of infection for antimicrobial compound efficacy studies against intracellular and extracellular forms of *Staphylococcus aureus*", Veterinary Microbiology, 101, 2004, pp. 253-262.
Blondeau, "New concepts in antimicrobial susceptibility testing: the mutant prevention concentration and mutant selection window approach", Veterinary Dermatology, 20(5-6), 2009, pp. 383-396.
Drlica, "The mutant selection window and antimicrobial resistance", Journal of Antimicrobial Chemotherapy, 52, 2003, pp. 11-17.
Jin-Ping, "In vitro antibacterial activity of fosfomycin in combination with 14 antimicrobial agents", Chinese Journal of Antibiotics, 30(4), 2005, pp. 233-237.
Database WPI, Week 198729, Thomson Scientific, London, GB; AN 1987-201980 XP002703975; 2 pages.
European Patent Office, International Search Report for International Patent Application No. PCT/EP2013/063310, dated Jul. 31, 2013, 4 pages.
European Patent Office, Written Opinion for International Patent Application No. PCT/EP2013/063310, dated Dec. 29, 2014, 4 pages.
International Bureau of WIPO, International Preliminary Report on Patentability for International Patent Application No. PCT/EP2013/063310, dated Dec. 31, 2014, 5 pages.
Mukherjee, et al., "Immunomodulatory and Therapeutic Potential of Enrofloxacin in Bovine Sub Clinical Mastitis," Asian-Australasian Journal of Animal Sciences, vol. 16, No. 6, Jun. 1, 2003, pp. 889-893.
Oliver, et al., "Influence of Prepartum Pirlimycin Hydrochloride or Penicillin-Novobiocin Therapy on Mastitis in Heifers During Early Lactation," Journal of Dairy Science, American Dairy Science Association, vol. 87, No. 6, Jun. 1, 2004, pp. 1727-1731.
Xiaohong, Jin et al,, "In vitro antibacterial activity of fosfomycin in combination with antimicrobial agents against *Escherichia coli*", Practical Preventive Medicine, Jun. 30, 2006, pp. 769-770, vol. 13, No. 3.

(Continued)

*Primary Examiner* — Traviss C McIntosh, III
(74) *Attorney, Agent, or Firm* — McBee Moore Woodward & Vanik IP, LLC

(57) ABSTRACT

The present invention relates to a pharmaceutical composition and methods of treating and/or preventing mastitis in non-human mammals. More particularly, the present invention relates to the treatment of mastitis in cows. The pharmaceutical composition comprises a mixture of a phosphonic acid and at least one antimicrobial.

19 Claims, No Drawings

(56) References Cited

OTHER PUBLICATIONS

Yang, YingYing et al., "In vitro antibacterial activity of fosfomycin combined respectively with nine antimicrobial agents against acinetobacter", Journal of Dalian Medical University, Jun. 30, 2011, pp. 294-296, vol. 33, No. 3.

Xiujie, Song et al., "Antibacterial activity of levolloxacin combined with fosfomycin against *Staphylococcus aureus*", The Chinese Journal of Clinical Pharmacology, Nov. 30, 2009, pp. 505-508, vol. 25, No. 6.

Kastoris, Antonia C. et al., "Synergy of fosfomycin with other antibiotics for Gram-positive and Gram-negative bacteria", European Journal of Clinical Pharmacology, Dec. 31, 2010, pp. 359-368, vol. 66.

Matsuura, "The combined effect of anti-microbial agents and fosfomycin against micro organism derived from mastitis" Kachiku-Eisei-Gaku-Zasshi (The magazine of Animal Hygiene), The Abstract of the 65th Annual meeting of The Japanese Society of Animal Hygiene, p. 27 (abstract), Nov. 2006.

Novelli, et al., "Clinical Chemotherapeutic Evaluation of Fosfomycin plus Amoxicillin (Co-fosfolactamine): A Prospective Double-blind Clinical Trial," Chemioterapia, (1984), vol. 3, No. 5: 281-285.

Zhu, et al., "Prevention and Treatments of Mastitis of Dairy Cow," Chinese Journal of Veterinary Medicine, (2008), vol. 42, No. 3: 40-45.

Lian, et al., "Synergy of fosfomycin sodium and other antimicrobial agents and the clinical application thereof," World Notes on Antibiotics, (2003), vol. 24, No. 1: 44-46.

Araki, et al., "Antimicrobial Activity of Amoxicillin and Other Penicillins against Clinical Isolates from Bovine Udders," Japanese Journal of Veterinary Science, (1985), vol. 47, No. 2: 321-323.

Xu, et al., "Studies on the Efficacy of Pirlimycin Hydrochloride for Mastitis Treatment and Milk Quality in Lactating Dairy Cows," China Dairy Cattle, (2011), vol. 8: 48-51.

Grif, et al., "In vitro activity of fosfomycin in combination with various antistaphylococcal substances," Journal of Antimicrobial Chemotherapy, (2001), vol. 48 :209-217.

Lai, "Effects of cefazolin sodium on mastitis in dairy cows," Yunnan Journal of Animal Science and Veterinary Medicine, (1993), vol. 1: 17-18.

\* cited by examiner

PHARMACEUTICAL COMPOSITIONS AND TREATMENT OF MASTITIS

FIELD OF INVENTION

The present invention relates to an intra-mammary pharmaceutical composition and method of treating or preventing mastitis in a non-human mammal.

BACKGROUND OF INVENTION

Bovine mastitis is one of the most common diseases in dairy cattle. Mastitis occurs when the udder becomes inflamed. Inflammation may be caused by many types of injury including infectious agents and their toxins, physical trauma or chemical irritants. Many microorganisms or bacteria have been identified as causing mastitis, but it is believed that serious cases of mastitis are in most instances caused by either of following pathogens, i.e. *Staphylococcus aureus, Streptococcus agalactiae, Streptococcus dysgalactiae, Streptococcus uberis* and *E. coli*.

The most common mastitis pathogens are found either in the udder (contagious pathogens) or the cow's surroundings (environmental pathogens). Contagious pathogens, such as *Streptococcus agalactiae* and *Staphylococcus aureus*, primarily colonize host tissue sites such as mammary glands, teat canals, and teat skin lesions and are generally spread from infected udders to healthy udders during the milking process. This can include through contaminated teatcup liners, milker's hands, paper or cloth towels used to wash or dry more than one cow, and possibly flies. Environmental pathogens, such as streptococci, enterococci, and coliform organisms, are commonly present within the cow's surroundings from sources such as cow feces, soil, plant material, bedding, or water; and infect by casual opportunistic contact with an animal. In all cases of mastitis, whatever the causal microorganism, the route of transmission of the pathogen into the udder is through the teat orifice and teat canal.

Mastitis causes compositional changes in milk, including an increase in somatic cell count (SCC). Milk from normal (uninfected) cows generally contain below 200,000 somatic cells/ml. An elevation in SCC, above 300,000 somatic cells/ml is abnormal and is an indication of inflammation of the udder. The types of somatic cells present in the milk change to mostly white blood cells, which add many proteolytic and lipolytic enzymes to milk. In addition, more blood serum leaks into the milk than usual. Dairy product quality defects resulting from mastitis are due to enzymatic breakdown of milk protein and fat. Casein, the major milk protein of high nutritional quality, declines and lower quality whey proteins increase which adversely impacts dairy product quality, such as cheese yield, flavor and quality. Protein breakdown in the milk can occur in milk from cows with clinical or subclinical mastitis due to the presence of proteolytic enzymes. Plasmin increases proteolytic activity more than 2-fold during mastitis. Plasmin and enzymes derived from somatic cells can cause damage to casein in the udder before milk removal. Deterioration of the milk protein may also continue during processing and storage of milk from infected cows. Other compositional changes in the milk include a decrease in potassium and calcium levels.

Mastitis costs the US dairy industry about 1.7-2 billion dollars annually or 11% of the total US milk production. The cost includes reduced milk production, discarded milk, replacement cows, medication, labor, and veterinary services. Currently, acute mastitis is treated with antibiotics, antiinflammatories and oxytocin. The treatments however are often consuming (sometimes several successive intra-mammary applications), expensive, and not fully efficacious. As such, there is a need for a treatment option and pharmaceutical composition which improves the efficacy of the current standard or provides acceptable efficacy with additional positive assets, for example, reduced milk withdrawal, reduced duration of treatment, and/or less costly treatment option.

SUMMARY OF THE INVENTION

If large bacterial populations are exposed to fosfomycin, a small fraction of 10 to $10^4$ CFU will still be able to form colonies on agar. Within the re-grown colonies, a large number of new foci of growth became visible, as could be demonstrated for *S. aureus* and *E. coli*. Such phenotypically adapted new clones (mutants) are the likely cause of massive re-growth, which is regularly observed in liquid cultures kept at the same fosfomycin concentration. This process of adaptation needs to be prevented to effectively gain control over the large pathogen population. To our greatest surprise, small quantities of either enrofloxacin, cephazolin, pirlimicin or amoxicillin, e.g., could completely inhibit this step of differentiation in response to drug-selective pressure. Thus, the bactericidal component of fosfomycin activity can unfold optimally, and clonal expansion of persisting variants is blocked at clinically achievable drug concentrations. Such synergistic enhancement of antibiotic efficacy could subsequently be observed in animals, first in a mouse mastitis model and, thereafter, in infected udders of cattle. This antibacterial activity was formulated, preserved and released from the pharmaceutical formulations revealed below.

DETAILED DESCRIPTION OF THE PREFERRED EMBODIMENTS

The present invention is directed to pharmaceutical formulations and the use of these pharmaceutical formulations to prevent or treat mastitis in a non-human milk-producing mammal.

According to an aspect of the present invention, an intra-mammary pharmaceutical composition for use in the treatment or prevention of mastitis in a non-human mammal is provided, comprising a pharmaceutical composition of a phosphonic acid and at least one antimicrobial.

According to an embodiment of the pharmaceutical composition of the present invention, the phosphonic acid is selected from the group consisting of fosfomycin, fosmidomycin, and alafosfalin.

According to a preferred embodiment of the pharmaceutical composition of the present invention, the phosphonic acid is fosfomycin.

According to another embodiment of the pharmaceutical composition of the present invention, the antimicrobial is selected from the group consisting of a quinolone, β-lactam, and macrolide-streptogramin-lincosamide.

According to a preferred embodiment of the pharmaceutical composition of the present invention, the antimicrobial is a quinolone. According to a more preferred embodiment of the pharmaceutical composition of the present invention, the quinolone is selected from the group consisting of benofloxacin, binfloxacin, cinoxacin, ciprofloxacin, clinafloxacin, danofloxacin, difloxacin, enoxacin, enrofloxacin, fleroxacin, gemifloxacin, ibafloxacin, levofloxacin, lomefloxacin, marbofloxacin, moxifloxacin, norfloxacin, ofloxacin, orbifloxacin, pazufloxacin, pradofloxacin, perfloxacin, temafloxacin, tosufloxacin, sarafloxacin, and sparfloxacin.

According to another preferred embodiment of the pharmaceutical composition of the present invention, the antimicrobial is a fluoroquinolone. According to a more preferred embodiment of the pharmaceutical composition of the present invention, the fluoroquinolone is selected from the group consisting of ciprofloxacin, enrofloxacin, moxifloxacin, and pradofloxacin.

According to an even more preferred embodiment of the pharmaceutical composition of the present invention, the quinolone is enrofloxacin.

According to another preferred embodiment of the pharmaceutical composition of the present invention, the antimicrobial is β-lactam. According to a more preferred embodiment of the pharmaceutical composition of the present invention, the β-lactam is selected from the group consisting of a penicillin, cephalosporin, carbapenem and penem, and β-lactamase inhibitor.

According to an even more preferred embodiment of the pharmaceutical composition of the present invention, the β-lactam is cephalosporin. According to a still even more preferred embodiment of the pharmaceutical composition of the present invention, the cephalosporin is cefazolin.

According to an even more preferred embodiment of the pharmaceutical composition of the present invention, the β-lactam is penicillin. According to a still even more preferred embodiment of the pharmaceutical composition of the present invention, the penicillin is amoxicillin.

According to another preferred embodiment of the pharmaceutical composition of the present invention, the antimicrobial is a macrolide-streptogramin-lincosamide. According to a more preferred embodiment of the pharmaceutical composition of the present invention, the macrolide-streptogramin-lincosamide is selected from the group consisting of a macrolide, lincomycin, clindamycin, and pirlimycin. According to an even more preferred embodiment of the pharmaceutical composition of the present invention, the macrolide-streptogramin-lincosamide is pirlymicin.

According to another aspect of the present invention, a method for treating mastitis is provided, comprising administering to a non-human mammal having mastitis an effective amount of a pharmaceutical composition comprising a phosphonic acid and at least one antimicrobial.

According to still another aspect of the present invention a method for preventing mastitis is provided, comprising administering to a non-human mammal an effective amount of a pharmaceutical composition comprising a phosphonic acid and at least one antimicrobial.

According to a respective embodiment of the methods of the present invention, the phosphonic acid is as defined in any one of the embodiments of the pharmaceutical composition mentioned before.

According to another respective embodiment of the methods of the present invention, the antimicrobial is as defined in any one of the embodiments of the pharmaceutical composition mentioned before.

According to another aspect of the present invention, a use of a pharmaceutical composition of a phosphonic acid and at least one antimicrobial for the treatment or prevention of mastitis on a non-human mammal is provided.

According to yet another aspect of the present invention, a use of a phosphonic acid and at least one antimicrobial for the manufacture of an intra-mammary pharmaceutical composition for the treatment or prevention of mastitis in a non-human mammal is provided. According to a preferred embodiment of the use for manufacture, a composition, preferably a pharmaceutical composition, of a phosphonic acid and at least one antimicrobial is used.

According to a respective embodiment of the uses of the present invention, the phosphonic acid is as defined in any one of the embodiments of the pharmaceutical composition mentioned before.

According to another respective embodiment of the uses of the present invention, the antimicrobial is as defined in any one of the embodiments of the pharmaceutical composition mentioned before.

I. Pharmaceutical Compositions a. Active Ingredients

In accordance with the present invention, the pharmaceutical composition used in this treatment comprises a mixture of a phosphonic acid in combination with at least one additional active ingredient comprising an antimicrobial. Suitable phosphonic acids include fosfomycin ([(2R,3S)-3-methyloxiran-2-yl]phosphonic acid), fosmidomycin and alafosfalin. A preferred phosphonic acid is fosfomycin.

The antimicrobial to be combined with fosfomycin can be any antimicrobial known in the pharmaceutical arts to be suitable for local treatment of mastitis (i.e., intra-mammary or intracisternal application). The antimicrobial may be selected from one or more of the following well-known classes of antimicrobials including: quinolones, preferably fluoroquinolones, β-lactams, and macrolide-streptogramin-lincosamide (MLS) antibiotics.

Suitable quinolones include benofloxacin, binfloxacin, cinoxacin, ciprofloxacin, clinafloxacin, danofloxacin, difloxacin, enoxacin, enrofloxacin, fleroxacin, gemifloxacin, ibafloxacin, levofloxacin, lomefloxacin, marbofloxacin, moxifloxacin, norfloxacin, ofloxacin, orbifloxacin, pazufloxacin, pradofloxacin, perfloxacin, temafloxacin, tosufloxacin, sarafloxacin, gemifloxacin, and sparfloxacin. Preferred fluoroquinolones include ciprofloxacin, enrofloxacin, moxifloxacin, danofloxacin, and pradofloxacin. Suitable naphthyridones include nalidixic acid.

Suitable β-lactams include penicillins, such as benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav (amoxicillin and clavulanic acid), azlocillin, carbenicillin, ticarcillin, mezlocillin, piperacillin; cephalosporins, such as cefalonium, cephalexin, cefazolin, cefapririn, cefquinome, ceftiofur, cephalothin, cefaclor, cefuroxime, cefamandole, defotetan, cefoxitin, ceftriaxone, cefotaxime, cefpodoxime, cefixime, ceftazidime, cefepime, cefpirome; carbapenems and penems such as imipenemi, meropenem, ertapenem, faropenem, doripenem, monobactams such as aztreonam (Azactam), tigemonam, nocardicin A, tabtoxinine-B-lactam; and β-lactamase inhibitors such as clavulanic acid, tazobactam, and sulbactam. Preferred β-lactams include penicillins, in particular amoxicillin, and cephalosporins, in particular, cefazolin.

Suitable MLS antibiotics include any macrolide, lincomycin, clindamycin, pirlimycin. A preferred lincosamide is pirlimycin.

Other antimicrobials include 2-pyridones, tetracyclines, sulfonamides, aminoglycoside, trimethoprim, dimetridazoles, erythromycin, framycetin, furazolidone, various pleuromutilins such as tiamulin, valnemulin, various, streptomycin, clopidol, salinomycin, monensin, halofuginone, narasin, robenidine, etc.

The fosfomycin, fosmidomycin or alafosfalin and the antimicrobial with which it is combined may be used in their free acid or base forms as well as in the form of an enantiomer, a pharmaceutically acceptable salt or adduct. The term pharmaceutically-acceptable refers to the relatively non-toxic, inorganic and organic acid and base addition salts and adducts. As used herein, when reference is made to a fosfomycin, fosmidomycin or alafosfalin and other antibiotic active ingredients, it is intended to include these pharmaceutically acceptable forms. Representative salts include, for example, the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Other such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. A fosfomycin, fosmidomycin or alafosfalin as well as antimicrobial contain one or more acidic functional groups and, thus, are capable of forming pharmaceutically-acceptable salts with pharmaceutically-acceptable bases. The term pharmaceutically-acceptable salts in these instances refer to the relatively non-toxic, inorganic and organic base addition salts of antimicrobials of the present invention. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, Trometamol (tris(hydroxymethyl)aminomethan), piperazine and the like. Some preferred pharmaceutically-acceptable salts include cefazolin sodium, pirlimycin hydrochloride, fosfomycin (di) sodium, fosfomycin calcium, and fosfomycin trometamol.

The pharmaceutical composition of the present invention may be an intra-mammary product or a systemic product. In one embodiment, the pharmaceutical composition is an intra-mammary product that is administered into the teat orifice when treating or preventing mastitis of a non-human mammal.

In one embodiment, the pharmaceutical composition comprises a mixture of fosfomycin in combination with at least one antimicrobial selected from the group consisting of enrofloxacin, cefazolin, pirlimycin, amoxicillin and combinations thereof. In another embodiment, the pharmaceutical composition comprises a mixture of fosfomycin and enrofloxacin. In yet another embodiment, the pharmaceutical composition comprises a mixture of fosfomycin and cefazolin. In a further embodiment, the pharmaceutical composition comprises a mixture of fosfomycin and pirlimycin. In still a further embodiment, the pharmaceutical composition comprises a mixture of fosfomycin and amoxicillin.

In accordance with the present invention, the pharmaceutical composition contains a pharmaceutically effective amount of a mixture of fosfomycin and at least one antimicrobial. As used herein, the term "pharmaceutically effective amount" refers to a dose sufficient to either prevent or treat mastitis in a subject to which the pharmaceutical composition is administered. The dose depends on the active ingredient(s), the animal being treated, the state of condition, and the severity of the conditions. The determination of those factors is well within the level of one skilled in the art.

In general, effective dosage will vary depending on the mode of administration. In an intra-mammary pharmaceutical composition, the ratio of fosfomycin to enrofloxacin is from 5:1 to 5:4 based on the free acids. In another embodiment of an intra-mammary pharmaceutical composition, the ratio of fosfomycin to cefazolin is from 5:1 to 5:4 based on the free acids. In yet another embodiment of an intra-mammary pharmaceutical composition, the ratio of fosfomycin to pirlimycin is from about 10:1 to 40:1 based on the free acid and free base, respectively.

The present invention is preferably prepared as an intra-mammary ointment, suspension, solution or gel.

II. Methods a. Method of Treatment

The pharmaceutical composition of the present invention may be used in the prevention or for the treatment of mastitis in an animal. Mastitis may be associated with several pathogens including *E. coli*, *Klebsiella* spp., *Enterobacter* spp., *Salmonella* spp., *Citrobacter* spp., *Serratia* spp., *Shigella* spp., *Edwardsiella* spp., *Hafnia* spp., *Morganella* spp., *Providencia* spp., *Yersinia* spp., *Staphylococcus aureus*, *Staphylococcus* spp., *Pseudomonas* spp., *Streptococcus agalactiae*, *Streptococcus dysgalactiae*, *Streptococcus* spp., *Enterococci*, *Corynebacterium* spp., *Arcanobacterium* spp., *Actinomyces* spp., *Mycobacterium* spp., *Prototheca* spp., *Mycoplasma* spp., and *Erwinia* spp., among others.

The pharmaceutical composition may be used for various applications with the application route and dosage regimen dictated by the frequency of milking and/or the condition of the mammary gland of the animal.

The pharmaceutical composition can be applied to all non-human milk producing mammals that need treatment or prevention of mastitis, such as cattle, camel, buffalo, goat or sheep, however it is especially important in ruminants that are used for milk production for human consumption such as cattle, buffalo, sheep, and goat.

Treatment of mastitis is curing or ameliorating an animal that has contracted mastitis, i.e. reducing at least one symptom of mastitis. Mastitis refers to inflammation of the mammary gland. Physical, chemical and usually bacteriological changes in the milk and pathological changes in the glandular tissue characterize it. The glandular changes often result in a number of symptomatic conditions such as, discoloration of the milk, the presence of clots and the presence of large numbers of leukocytes. Clinically, mastitis is seen as swelling, heat, pain and induration in the mammary gland often resulting in deformation of the udder. An inflamed udder can be visibly seen or determined through palpation of the udder. In many cases the diagnosis of subclinical infections has come to depend largely on indirect tests which depend on the leukocyte content of the milk (flakes, clots, or serous milk), at least 1 bacterium is detected in at least 100 µL of milk from the udder, elevated somatic cell count (SCC) usually higher than 300,000 cells/mL and/or the electrical conductivity of the milk is increased from normal. Prevention of mastitis means preventing the occurrence of the infection. Prevention also includes treatment of cows that do not exhibit any signs of mastitis but are in the presence of other cows that do have at least one sign of mastitis to minimize or prevent the transmission or potential transmission of mastitis from one cow to another.

The effectiveness of the pharmaceutical composition in treating mastitis of an animal is quantified as the percent of cleared mammary glands (i.e., 1 µL of milk is free from any bacteria). In one embodiment, the pharmaceutical composition clears at least 50% of the mammary glands of the animal. In another embodiment, the pharmaceutical composition clears from about 50% to about 90% of the mammary glands of the animal. In yet another embodiment, the pharmaceutical composition clears from about 70% to about 90% of the mammary glands of an animal.

The pharmaceutical composition may be administered intramammarily, through the teat orifice into the interior cavity of the mammary gland and its associated ductal system. The pharmaceutical composition may be in the form of an ointment, suspension, solution or gel. Alternatively, the pharmaceutical composition may also be administered systemically via intravenous, subcutaneous, and intramuscular administration.

The dose of the active ingredient combination for the treatment of one udder quarter may contain from about 100 to about 3000 mg of fosfomycin or fosfomycin salt (on a free acid basis) preferably from about 500 to about 2000 mg, in combination with from about 50 to about 1000 mg, preferably from about 200 to about 800 mg, of a B lactam antibiotic, preferably a cephalosporin, more preferably cefazolin, calculated as free acid. In another embodiment, the dose of the active ingredient combination for the treatment of one udder quarter may contain from about 100 to about 3000 mg of fosfomycin (on a free acid basis), preferably from about 500 to about 2000 mg, in combination with from about 50 to about 1000 mg, preferably from about 200 to about 800 mg of a quinolone, preferably a fluoroquinolone, more preferably enrofloxacin, calculated as free acid. In yet another embodiment, the dose of the active ingredient combination for the treatment of one udder quarter may contain from about 100 to about 3000 mg of fosfomycin or fosfomycin salt (on a free acid basis) preferably from about 500 to about 2000 mg, in combination with from about 10 to about 500 mg, preferably from about 25 to about 100 mg of a lincosamide, preferably pirlimycin, calculated as free base.

The dose of the active ingredient combination (treatment or prevention) may be administered repeatedly over a period of from two to eight days. In one embodiment, the dose is administered once or twice a day over a period of two to eight days. In another embodiment, the dose of the active ingredient combination is administered once or twice a day over a period of four to six days. It is believed that the precise combination of dosage and timing will be subject to a wide range of variation and that numerous combinations effective in treating or preventing a disease can be readily established by those of ordinary skill in the art in view of the present disclosure.

In view of the above, it will be seen that the several objects of the invention are achieved and other advantageous results attained. As various changes could be made in the above formulations, products, and processes without departing from the scope of the invention, it is intended that all matter contained in the above description and shown in the accompanying tables shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The following examples are simply intended to further illustrate and explain the present invention. The examples, therefore, should not be regarded as limiting the scope of the invention or manner in which it may be practiced.

EXAMPLES

Example 1

| Ingredient name (common or chemical) | Concentrations mg/10 ml |
|---|---|
| Cefazolin Sodium** | 419.4 |
| Fosfomycin Sodium*** | 1318.9 |
| Cetearyl alcohol | 200.0 |
| White soft paraffin | 1000.0 |
| Liquid paraffin | 6461.7 |
| | 9400.0* |

*9400 mg is equal to 10 ml
**419.4 mg Cefazolin Sodium is equal to 400 mg Cefazolin free acid
***1318.9 mg Fosfomycin Sodium is equal to 1000 mg Fosfomycin free acid Liquid paraffin, white soft paraffin and cetearyl alcohol were melted in a suitable vessel. The mixture was sterilized by heating the excipients for 120 minutes to 160° C. The mixture was then cooled to 40-50° C. and sterile and micronized cefazolin sodium and fosfomycin sodium were added under sterile conditions. The mixture was then homogenized for 15 minutes. 10 ml of the finished pharmaceutical composition was filled into a sterile injector under sterile conditions.

Example 2

| Ingredient name (common or chemical) | Concentrations mg/10 g |
|---|---|
| Cefazolin free acid | 400.0 |
| Fosfomycin Trometamol **** | 1877.2 |
| Cetearyl alcohol | 250.0 |
| Sodium cetearyl aryl sulphate (90:10) | |
| White soft paraffin | 1100.0 |
| Light liquid paraffin | 6372.8 |
| | 10000.0 |

**** 1877.2 mg Fosfomycin Trometamol are equal to 1000 mg Fosfomycin free acid

Liquid paraffin, white soft paraffin and cetearyl alcohol sodium cetearyl aryl sulphate were melted in a suitable vessel. The mixture was then sterilized by heating the excipients for 120 minutes to 160° C. The mixture was then cooled to 40-50° C. and sterile and micronized cefazolin and fosfomycin trometamol were added under sterile conditions. The mixture was then homogenized for 15 minutes. 10 g of the finished pharmaceutical composition was filled into a sterile injector under sterile conditions.

Example 3

| Ingredient name (common or chemical) | Concentrations mg/10 ml |
|---|---|
| Enrofloxacin | 400.0 |
| Fosfomycin Sodium** | 1318.9 |
| Cetearyl alcohol | 250.0 |
| Sodium cetearyl aryl sulphate (90:10) | |

-continued

| Ingredient name (common or chemical) | Concentrations mg/10 ml |
|---|---|
| White soft paraffin | 1200.0 |
| Liquid paraffin | 6231.1 |
| | 9400.0* |

*9400 mg are equal to 10 ml
**1318.9 mg Fosfomycin Sodium are equal to 1000 mg Fosfomycin free acid Liquid paraffin, white soft paraffin and cetearyl alcohol sodium cetearyl aryl sulphate was melted in a suitable vessel. The mixture was sterilized by heating the excipients for 120 minutes to 160° C. The mixture was then cooled to 40-50° C. and sterile and micronized enrofloxacin and fosfomycin sodium were added under sterile conditions. The mixture was then homogenized for 15 minutes. 10 ml of the finished pharmaceutical composition was filled into a sterile injector under sterile conditions.

Example 4

| Ingredient name (common or chemical) | Concentrations mg/10 ml |
|---|---|
| Enrofloxacin | 800.0 |
| Fosfomycin Sodium** | 2637.8 |
| Cetearyl alcohol | 200.0 |
| White soft paraffin | 700.0 |
| Light liquid paraffin | 5632.2 |
| | 9970.0* |

*9970.0 mg are equal to 10 ml
**2637.8 mg Fosfomycin Sodium are equal to 2000 mg fosfomycin free acid Liquid paraffin, white soft paraffin and cetearyl alcohol were melted in a suitable vessel. The mixture was sterilized by heating the excipients for 30 minutes to 180° C. The mixture was then cooled to 40-50° C. and sterile and micronized enrofloxacin and fosfomycin sodium were added under sterile conditions. The mixture was then homogenized for 15 minutes. 10 ml of the finished pharmaceutical composition was filled into a sterile injector under sterile conditions.

Example 5

| Ingredient name (common or chemical) | Concentrations mg/10 ml |
|---|---|
| Pirlimycin HCl x H$_2$O** | 56.6 |
| Fosfomycin Sodium*** | 1318.9 |
| Sodium citrate | q.s.* |
| Water for Injections | ad 10 ml |

*to adjust the pH to 7.3
**56.6 mg Pirlimycin Hydrochloride (x H$_2$O) is equal to 50 mg Pirlimycin free base
***1318.9 mg Fosfomycin Sodium are equal to 1000 mg Fosfomycin free acid A suitable vessel is filled with water for injections. Pirlimycin HCl and fosfomycin sodium are dissolved under stirring. The pH of the solution is adjusted to 7.3 with sodium citrate. The solution is stirred for additional 15 minutes. The solution is then filtered through a sterile filter in a sterilized tank.
10 ml of the sterile solution in filled into sterile injectors under sterile conditions.

Example 6—In Vivo Mouse Data

This study was performed using a *S. aureus* mouse mastitis model (MMM) established at the University of Sherbrooke, Canada (Brouillette et al., 2004), which is hereby incorporated by reference.

Both the abdominal mammary glands (L4 and R4) of lactating CD-1 mice were intramammarily infected with 100 CFU (colony forming units) of *Staphylococcus aureus* Newbould 305 (ATCC 29740).

The mice were treated intramammarily (IMAM) with enrofloxacin, fosfomycin and a combination of enrofloxacin and fosfomycin as detailed in Table 1 four hours after inoculation. Each treatment group contained at least 3 mice (6 glands). Fourteen hours later (18 hours after inoculation) mice were sacrificed, mammary glands were harvested and the CFU content evaluated by plating 10-fold serial dilutions of mammary gland homogenates. The CFU content was expressed as $\log_{10}$ count. The detection limit was 200 CFU/g of gland. Glands with less than 200 CFU/g were regarded as cleared of *S. aureus* (see Table 1).

For each treatment group median $\log_{10}$ reductions of CFU were determined by subtracting the median $\log_{10}$ CFU value of the respective group from the median $\log_{10}$ CFU value of the untreated control group.

TABLE 1

| Trial | Active | Dose in µg | Median CFU $\log_{10}$ | $\log_{10}$ CFU reduction | Cleared glands % |
|---|---|---|---|---|---|
| A | Enrofloxacin | 0 | 8.2 | / | 0 |
|   |   | 100 | 6.8 | 1.41 | 0 |
| B | Fosfomycin | 0 | 8.3 | / | 0 |
|   |   | 500 | 5.0 | 3.3 | 0 |
|   |   | 1000 | 3.2 | 5.1 | 0 |
| C | Enrofloxacin | 0 | 8.6 | / | 0 |
|   | (100 µg) + | 500 | 1.1 | 7.5 | 37 |
|   | Fosfomycin | 1000 | 0 | 8.6 | 83 |

As can be seen from Table 1, the intra-mammary instillation of 100 microgram enrofloxacin reduces the median CFU content by 1.4 $\log_{10}$ but does not eliminate the infection from the infected glands. Also the intra-mammary instillation of 500 or 1000 microgram fosfomycin reduces the median CFU content by 3.3 or 5.1 $\log_{10}$ but does not eliminate the infection from the infected glands. However synergistic efficacy is shown for the combined enrofloxacin-fosfomycin treatment as the intra-mammary instillation of 500 and 1000 microgram fosfomycin simultaneously with 100 microgram enrofloxacin eliminates the infection from 37% and 83% of the infected glands, respectively.

Example 7—Enrofloxacin-Fosfomycin MPC, Cefazolin-Fosfomycin MPC, Pirlimycin-Fosfomycin MPC The mutant prevention concentration (MPC) is the drug concentration that blocks the growth of the least susceptible, single-step mutant. Above this concentration, cell growth requires the presence of two or more resistance mutations. Since two concurrent mutations are expected to arise rarely, resistance is expected to develop rarely when drug concentrations are kept above the MPC. For further information regarding the MPC, it is by way of example referred to Drlica, K. (2003). The mutant selection window and antimicrobial resistance. *Journal of Antimicrobial Chemotherapy*, 52(1), 11-17; and to Blondeau, J. M. (2009). New concepts in antimicrobial susceptibility testing: the mutant prevention concentration and mutant selection window approach. *Veterinary dermatology*, 20(5-6), 383-396.

The MPC of enrofloxacin against *S. aureus* is 3 µg/mL, while the MPC of fosfomycin against *S. aureus* amounts to 1500 µg/mL. Synergistic activity, i.e., inhibition of visible growth of *S. aureus* over 14 days, is shown for the combination enrofloxacin-fosfomycin as the MPC of enrofloxacin and fosfomycin in combination is as low as 0.12 µg/mL and 100 µg/mL of enrofloxacin and fosfomycin, respectively.

The MPC of cefazolin against *S. aureus* is 1.25 µg/mL, while the MPC of fosfomycin against *S. aureus* amounts to 1500 µg/mL. Synergistic activity, i.e., inhibition of visible growth of *S. aureus* over 14 days, is shown for the combination cefazolin-fosfomycin as the MPC of cefazolin and fosfomycin in combination is as low as 0.05 µg/mL and 100 µg/mL of cefazolin and fosfomycin, respectively. The MPC of cefazolin against *E. coli* is 64 µg/mL, while the MPC of fosfomycin against *E. coli* amounts to 200 µg/mL. Synergistic activity, i.e., inhibition of visible growth of *E. coli* over 14 days, is shown for the combination cefazolin-fosfomycin as the MPC of cefazolin and fosfomycin in combination is as low as 0.8 µg/mL and 5 µg/mL of cefazolin and fosfomycin, respectively.

The MPC of pirlimycin against *S. aureus* is 2 µg/mL, while the MPC of fosfomycin against *S. aureus* amounts to 1500 µg/mL. Synergistic activity, i.e., inhibition of visible growth of *S. aureus* over 14 days, is shown for the combination pirlimycin-fosfomycin as the MPC of pirlimycin and fosfomycin in combination is as low as 0.1 µg/mL and 100 µg/mL of pirlimycin and fosfomycin, respectively.

Example 8—Cefazolin-Fosfomycin In-Vivo Mouse Data

The same experiment as in Example 1 was run with cefazolin rather than enrofloxacin.

The intra-mammary instillation of 50 or 100 microgram cefazolin reduces the median CFU content by 4.5 or 5.1 $\log_{10}$, respectively, but does not eliminate the infection from the infected glands. Also the intra-mammary instillation of 100, 500 or 1000 microgram fosfomycin reduces the median CFU content by 2.0, 3.3 or 5.1 $\log_{10}$ but does not eliminate the infection from the infected glands. However synergistic efficacy is shown for the combined cefazolin-fosfomycin treatment as the intra-mammary instillation of 250, 500 and 1000 microgram fosfomycin simultaneously with 50 microgram cefazolin eliminates the infection from 100, 83 and 100% of the infected glands, respectively, and the intra-mammary instillation of 100, 500 and 1000 microgram fosfomycin simultaneously with 100 microgram cefazolin eliminates the infection from 14, 57, and 100% of the infected glands, respectively.

Example 9—Amoxicillin-Fosfomycin In-Vivo Mouse Data

The same experiment as in Example 1 was run with amoxicillin rather than enrofloxacin.

The intra-mammary instillation of 100 microgram amoxicillin reduces the median CFU content by 1.6 $\log_{10}$ but does not eliminate the infection from the infected glands. Also the intra-mammary instillation of 1000 microgram fosfomycin reduces the median CFU content by 5.1 $\log_{10}$ but does not eliminate the infection from the infected glands. However synergistic efficacy is shown for the combined amoxicillin treatment as the intra-mammary instillation of 1000 microgram fosfomycin simultaneously with 100 microgram amoxicillin eliminates the infection from 87% of the infected glands.

Example 10—Pirlimycin-Fosfomycin In-Vivo Mouse Data

The same experiment as in Example 1 was run with pirlimycin rather than enrofloxacin.

In mice with mastitis caused by *S. aureus* infection, the intra-mammary instillation of 10 microgram pirlimycin reduces the median CFU content by 3.3 $\log_{10}$ but does not eliminate the infection from the infected glands. Also the intra-mammary instillation of 100, 500 and 1000 microgram fosfomycin reduces the median CFU content by 2.0, 3.3 or 5.1 $\log_{10}$ but does not eliminate the infection from the infected glands. However synergistic efficacy is shown for the combined pirlimycin treatment as the intra-mammary instillation of 100, 500 and 1000 microgram fosfomycin simultaneously with 10 microgram pirlimycin eliminates the infection from 50, 60 and 100% of the infected glands, respectively.

Example 11—Cefazolin-Fosfomycin In-Vivo Cattle Data—Clinical Mastitis

In a first field-study, dairy cattle with clinical mastitis were treated under field conditions with either cefazolin, fosfomycin or a combination of both compounds. As soon as clinical symptoms of mastitis such as udder swelling, udder pain and abnormal milk were observed, the compounds, formulated into a paraffin based ointment, were instilled randomly in 110 diseased udder quarters, either 400 mg cefazolin per quarter (in 35 quarters), or 1000 mg fosfomycin per quarter (in 37 quarters), or 400 mg cefazolin together with 1000 mg fosfomycin per quarter (in 38 quarters). The diseased quarters were treated with this ointment three consecutive times with an interval of 24 hours between each application. When a milk sample was taken from the diseased udder quarters before the treatment for the diagnosis of mastitis infection, pathogenic bacteria typical of clinical mastitis were isolated, i.e. *Streptococus uberis, Staphylococus aureus, Escherichia coli*, other streptococci and mixed infections of the aforementioned species. Milk samples were taken again approximately 1 week, 2 weeks and 3 weeks following treatment. Diseased udder quarters were considered cured when the clinical symptoms of mastitis had disappeared within one week without requiring a new antibiotic treatment and when the causative pathogenic bacterium, found in the diagnostic milk sample shortly before treatment, could not be isolated from any of the milk samples taken from one to three weeks following treatment. The cure rate of mastitis infection was higher in the udder quarters treated with the combination ointment (cefazolin together with fosfomycin), i.e. $17/38$ (45%), than in the quarters treated with the ointment containing cefazolin alone ($11/35$, 31%) or fosfomycin alone ($13/37$, 35%).

Example 12—Cefazolin-Fosfomycin In-Vivo Cattle Data—Subclinical Mastitis

In another field trial, dairy cattle with subclinical mastitis, i.e. persistent, chronic udder infections caused by *Staphylococcus aureus*, were treated with either cefazolin, fosfomycin or a combination of both compounds. Lactating cows producing milk with an increased Somatic Cell Count (SCC higher than 300,000 cells per mL), a key parameter for udder inflammation and an indicator of deteriorated milk quality, were screened for *S. aureus* infection. Upon confirmation of the infection, the compounds, formulated into a paraffin based ointment, were instilled randomly in 132 affected udder quarters, either 400 mg cefazolin per quarter (in 43 quarters), or 1000 mg fosfomycin per quarter (in 47 quarters), or 400 mg cefazolin together with 1000 mg fosfomycin per quarter (in 42 quarters). The affected quarters were treated with this ointment six consecutive times with an interval of 12 hours between each application. Milk samples were taken approximately 3 and 4 weeks following treatment. Infected udder quarters were considered cured when *S. aureus*, found in the diagnostic milk sample shortly before treatment, could not be isolated anymore from the milk samples taken 3 and 4 weeks later. The cure rate of *S. aureus* infection was higher in the udder quarters treated with the combination ointment (cefazolin together with fosfomycin), i.e. $^{28}/_{42}$ (67%), than in the quarters treated with the ointment containing cefazolin alone ($^{20}/_{43}$, 46%) or fosfomycin alone ($^{27}/_{47}$, 57%). Following treatment, the level of udder inflammation, as measured by the Somatic Cell Count in the milk samples post treatment, was lower in the udders treated with the cefazolin-fosfomycin combination (46% of milk samples with a SCC lower than 300,000 cells/mL) than in udders treated with cefazolin alone (30% of milk samples with a SCC lower than 300,000 cells/mL) or with fosfomycin alone (24% of milk samples with a SCC lower than 300,000 cells/mL). In addition, among the cured quarters there were also more quarters from which the level of milk inflammation had returned to normal (SCC lower than 300,000 cells per mL) when the cefazolin-fosfomycin combination treatment had been applied ($^{15}/_{42}$, 36%) compared to treatment with cefazolin alone ($^{10}/_{43}$, 23%) or with fosfomycin alone ($^{9}/_{47}$, 19%).

In conclusion, dairy cattle with clinical or subclinical mastitis are better cured by a combination of cefazolin and fosfomycin than by the single compounds given at the same dose, thus demonstrating synergy of the combination compared to the single compounds.

The invention claimed is:

1. An intra-mammary pharmaceutical composition for use in the treatment or prevention of mastitis in a non-human mammal, comprising a pharmaceutical composition of a phosphonic acid with a dosage of 500 to about 2000 mg and at least one antimicrobial with a dosage of about 10 to about 1000 mg,
wherein the phosphonic acid is selected from the group consisting of fosfomycin, alafosfalin, and pharmaceutically acceptable salt thereof, and
wherein the antimicrobial is selected from the group consisting of enrofloxacin, moxifloxacin, pradofloxacin, β-lactams, and macrolide-streptogramin-lincosamides, or a pharmaceutically acceptable salt thereof.

2. The composition of claim 1, wherein the antimicrobial is a β-lactam with a dosage of about 200 to about 800 mg.

3. The composition of claim 2, wherein the β-lactam is selected from the group consisting of a penicillin, cephalosporin, carbapenem and penem, and β-lactamase inhibitor.

4. The composition of claim 3, wherein the β-lactam is cephalosporin.

5. The composition of claim 4, wherein the cephalosporin is cefazolin in a dosage of about 200 mg to about 800 mg.

6. The intra-mammary pharmaceutical composition according to claim 4, wherein the phosphonic acid is fosfomycin or fosfomycin salt and wherein the cephalosporin is in a dosage of about 200 to about 800 mg.

7. The intra-mammary pharmaceutical composition according to claim 4, wherein the cephalosporin is cefazolin or a pharmaceutically acceptable salt thereof and wherein the phosphonic acid is fosfomycin or a pharmaceutically acceptable salt thereof.

8. The intra-mammary pharmaceutical composition according to claim 4, wherein the cephalosporin is cefazolin.

9. The composition of claim 3, wherein the β-lactam is penicillin.

10. The composition of claim 1, wherein the antimicrobial is a macrolide-streptogramin-lincosamide with a dosage of about 25 to about 100 mg.

11. A method for treating mastitis comprising administering to one udder quarter of a non-human mammal having mastitis the pharmaceutical composition according to claim 1.

12. The intra-mammary pharmaceutical composition according to claim 1, comprising a macrolide-streptogramin-lincosamide selected from the group consisting of a macrolide, lincomycin, clindamycin, and pirlimycin.

13. The intra-mammary pharmaceutical composition according to claim 1, wherein the phosphonic acid is fosfomycin or a pharmaceutically acceptable salt thereof.

14. The intra-mammary pharmaceutical composition according to claim 13, wherein the antimicrobial is amoxicillin or a pharmaceutically acceptable salt thereof.

15. The intra-mammary pharmaceutical composition according to claim 1, wherein the antimicrobial is enrofloxacin or a pharmaceutically acceptable salt thereof.

16. The intra-mammary pharmaceutical composition according to claim 1, wherein the antimicrobial is macrolide-streptogramin-lincosamide or a pharmaceutically acceptable salt thereof.

17. The intra-mammary pharmaceutical composition according to claim 16, wherein the macrolide-streptogramin-lincosamide is pirlimycin.

18. The intra-mammary pharmaceutical composition according to claim 1, wherein the composition has a synergistic effect.

19. The intra-mammary pharmaceutical composition according to claim 1, wherein the phosphonic acid is alafosfalin or a pharmaceutically acceptable salt thereof.

* * * * *